(12) United States Patent
Thorne et al.

(10) Patent No.: US 10,800,556 B2
(45) Date of Patent: Oct. 13, 2020

(54) METHODS FOR PREPARING AUTOLOGOUS BLOOD EYE DROPS

(71) Applicant: Thorne Intellectual Property Holdings, LLC, Bountiful, UT (US)

(72) Inventors: Gale Harrison Thorne, Bountiful, UT (US); Gale Harrison Thorne, Jr., Bountiful, UT (US)

(73) Assignee: THORNE INTELLECTUAL PROPERTY HOLDINGS, LLC, Bountiful, UT (US)

(*) Notice: Subject to any disclaimer, the term of this patent is extended or adjusted under 35 U.S.C. 154(b) by 0 days.

(21) Appl. No.: 16/501,534

(22) Filed: Apr. 25, 2019

(65) Prior Publication Data

US 2020/0130873 A1    Apr. 30, 2020

Related U.S. Application Data

(63) Continuation-in-part of application No. 16/350,279, filed on Oct. 25, 2018, now Pat. No. 10,555,872.

(51) Int. Cl.
| | |
|---|---|
| *A61J 1/00* | (2006.01) |
| *B65B 3/00* | (2006.01) |
| *B25J 21/02* | (2006.01) |
| *A61B 50/33* | (2016.01) |
| *A61J 1/05* | (2006.01) |
| *B65B 3/04* | (2006.01) |
| *A61B 50/00* | (2016.01) |

(52) U.S. Cl.
CPC .............. *B65B 3/003* (2013.01); *A61B 50/33* (2016.02); *A61J 1/05* (2013.01); *B25J 21/02* (2013.01); *B65B 3/04* (2013.01); *A61B 2050/005* (2016.02)

(58) Field of Classification Search
CPC .......... A61J 1/2096; A61J 1/2079; A61J 1/05; A61B 50/30; A61B 50/33; A61B 2050/314; A61B 2050/005; B65B 3/003; B65B 3/04; B25J 21/02
USPC .................................................. 206/570, 370
See application file for complete search history.

(56) References Cited

U.S. PATENT DOCUMENTS

| | | | | |
|---|---|---|---|---|
| 3,690,315 A | * | 9/1972 | Chittenden | A61F 5/441 604/324 |
| 4,146,153 A | * | 3/1979 | Bailen | A61J 1/2089 222/83 |
| 5,707,173 A | * | 1/1998 | Cottone | A61M 5/3205 206/366 |
| 6,164,044 A | * | 12/2000 | Porfano | B65B 55/10 422/28 |

(Continued)

*Primary Examiner* — Steven A. Reynolds
(74) *Attorney, Agent, or Firm* — Gale H. Thorne

(57) ABSTRACT

A convenience kit for sterilizing and delivering liquids into the safety of a sterile environment inside a plastic bag (which can be disposed in a field environment) wherein a so sterilized liquid is dispensed into a vessel which is capped and sealed before removal from the bag. The convenience kit can be provided in a solitary format or, as a subkit combined with other associated items in a more inclusive convenience kit. In short, convenience kits made according to the present invention provide opportunity for accomplishing an aseptic liquid sterilizing transfer, a task which is commonly associated with on-hand capability of a laminar flow hood, in field environments and other areas which are remote from facilities having laminar flow hoods.

17 Claims, 11 Drawing Sheets

(56) References Cited

U.S. PATENT DOCUMENTS

| | | | | |
|---|---|---|---|---|
| 8,056,719 B2* | 11/2011 | Porret | ............... | A61L 2/26 |
| | | | | 206/439 |
| 8,286,791 B2* | 10/2012 | Finke | ............... | A61M 5/008 |
| | | | | 206/366 |
| 8,449,521 B2* | 5/2013 | Thorne, Jr. | ............... | A61J 1/16 |
| | | | | 206/570 |
| 9,149,939 B2* | 10/2015 | Zambaux | ............... | B25J 21/02 |
| 9,636,444 B2* | 5/2017 | Burbank | ............... | A61M 1/1656 |
| 9,937,288 B2* | 4/2018 | Wright | ............... | A61M 5/14546 |
| 10,555,872 B1* | 2/2020 | Thorne | ............... | A61J 1/2086 |
| 2015/0078961 A1* | 3/2015 | Opie | ............... | A61L 2/26 |
| | | | | 422/28 |

\* cited by examiner

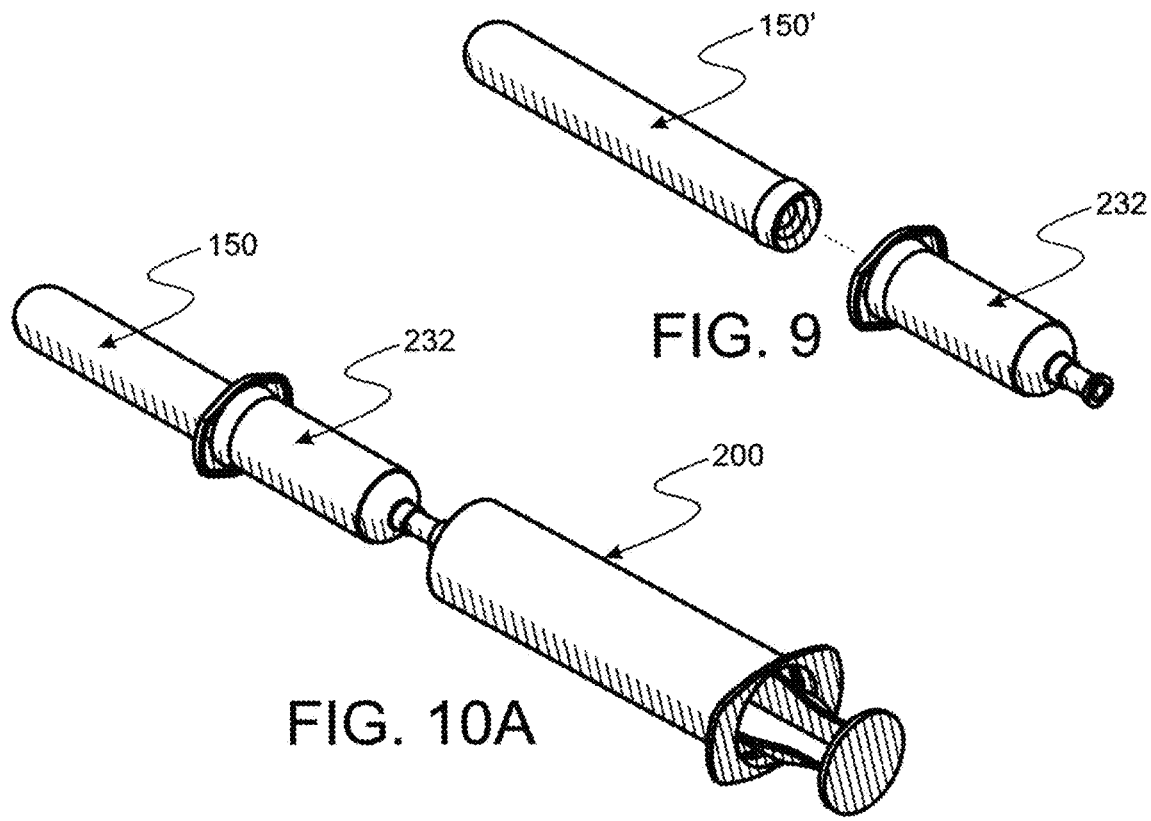
FIG. 9
FIG. 10A
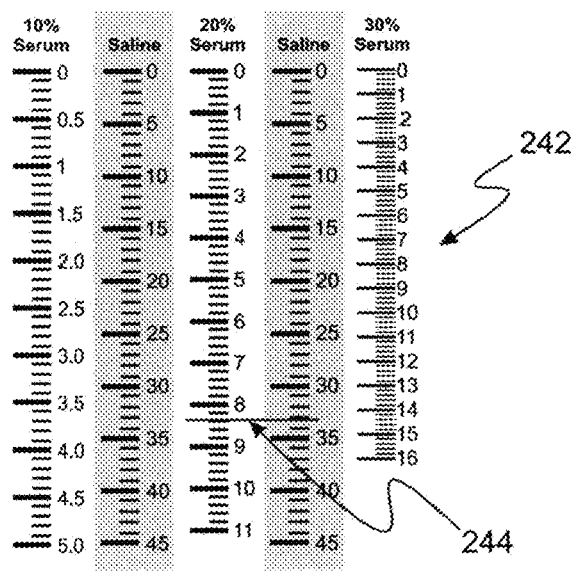
FIG. 12

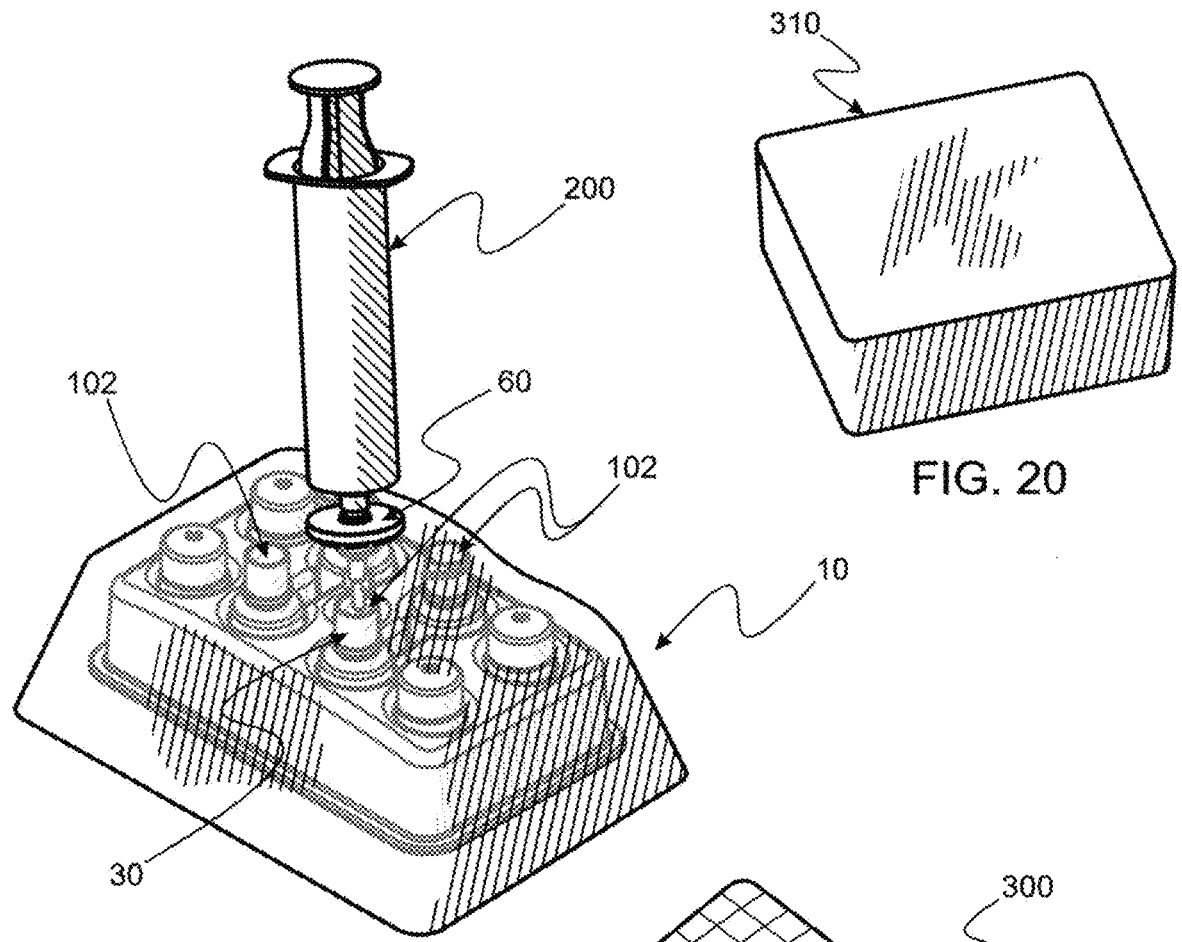
FIG. 16
FIG. 20
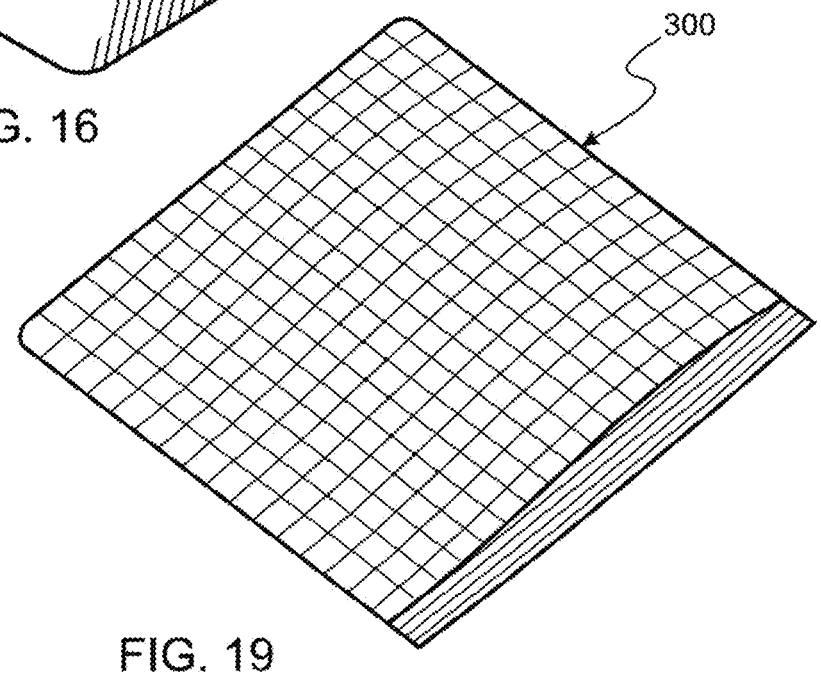
FIG. 19

METHODS FOR PREPARING AUTOLOGOUS BLOOD EYE DROPS

CONTINUATION-IN-PART

This Patent Application is a CONTINUATION-IN-PART of U.S. patent application Ser. No. 16/350,279 filed by Gale H. Thorne, et al. (Thorne 279). Oct. 25, 2018 and titled CONVENIENCE KITS FOR ASEPTIC STERILIZING AND DISPENSING.

FIELD OF INVENTION

This invention relates generally to methods for medical procedures involving liquid transfer, sterilization and mixing in a field environment to produce a sterile autologous blood eye drop product. It is also particularly related to kits and to methods which employ preassembled parts to provide a sterile product without requiring confines of a laminar flow hood.

BACKGROUND AND DESCRIPTION OF RELATED ART

Conventionally, mixing and formulation of medications is a pharmacy or other medical laboratory performed function most often involving use of laminar flow hoods and strict aseptic technique to maintain sterility. In pharmacies, medical solutions are often passed through a medical grade sterilizing filter to assure an aseptic condition. Resulting products from these facilities are highly regarded and widely used in hospitals and other clinical facilities.

However, today, a significant portion of medical practice takes place outside sophisticated medical institutions. As an example, a new and very effective eye-wash technology is based upon mixing autologous blood serum with normal saline in exacting proportions. Commonly, blood is drawn from patients in a wide range of areas remote from pharmacies and laboratories. The expense and inconvenience of relying on such facilities to sterilize and mix is prohibitive, negatively affecting broader application of this promising technology. Thus, there exists a severe contemporary need for a process or methodology, not currently available commercially, which can, with appropriate safety and efficacy, provide such sterilizing, dispensing and mixing to produce sealed containers of autologous blood eye drops in a field environment.

Convenience kits have become commonly used appliances for a number of reasons. First, a convenience kit is specifically made for a given application. Contents of each such kits are prepared and provided in a form which generally reduces procedure steps and improves efficiency. Second, such kits can provide additional safety such as the kit disclosed in U.S. Pat. No. 9,449,521, titled METHODS FOR MAKING AND USING A VIAL SHIELDING CONVENIENCE KIT, issued May 28, 2013, which proved effective in providing additional safety to technicians and patients by keeping hazardous drug fumes and liquid fully contained.

Vial and bottle filling into containers disposed within a plastic bag is also known in medical art. An example of such a process is provided in U.S. Pat. No. 9,140,939, allowed Oct. 6, 2015 to Jean-Pascal Zambaux (Zambaux) titled DISPOSABLE ISOLATOR COMPRIANIG MEANS FOR FILLING CONTAINERS. However, the process, as disclosed in Zambaux, has been abandoned in the United States due to experience of contamination in source liquid used for filling without further sterilization. Such contamination has been found to be in liquid distributed to a plurality of containers, resulting in a spread of infection. For this reason, compounding pharmacies are now commonly employed for filling medical vials and bottles through sterilizing filters. Relative to the instant method of the current invention, Zambaux is also deficient for being used for a portable all environment convenience kit because no method for capping and thereby protecting sterile state of liquid in bottles and vials is taught.

As indicated supra, use of sterilizing filters in now well known and accepted. U.S. Pat. No. 9,636,444 titled FILTRATION SYSTEM FOR PREPARATION OF FLUIDS FORM MEDICAL APPLICATIONS allowed to Jeffrey H. Burbank, et al. (Burbank) allowed May 2, 2017 discloses such use, but, as is the case of Zambaux, does not disclose filling and capping within a bag to protect a sterile state when removed therefrom.

TERMS AND DEFINITIONS

Following is a list of terms and associated definitions which are provided for clarity and understanding when used to disclose precepts of the instant invention:

contaminating environment, n: substance surrounding comprising freely moving masses which communicate with an unshielded substance to negatively affect the substance SAL
conventional adj: sanctioned by general custom; commonplace; ordinary
dead space, n: a volume of inaccessible fluid which is retained within a device after a procedure
digital, adj: relating to, or done with thumb or fingers
distal, adj: a distance relative to a cited object; opposite of proximal
ETO, n: acronym for ethylene oxide, a powerful sterilizing agent
field of use, n: a location in an uncontrolled environment in which potentially contaminating health-hazardous materials are present.
filter, n: a product material having a sufficiently small porous matrix to impede passage there through of a particulate of predetermined size; a medical grade sterilizing filter generally has a 0.2 micron pore size.
filter component, n: A housing, for a filter, having a a pair of opposing fittings providing communicating conduits to and from the filter.
fitting, n: a medical connector
insulated wrap, n: a flexible container which may be a bag or folded shield which is sealed to provide a container in which enclosed parts can be maintained at a reduced temperature
kit, n: a group of parts, provided within a single package for a designated use laminar flow hood, n: (a fume hood) a work-place enclosure in which purified air flow is directed so as to prevent contamination of sterile materials by airborne organisms. It should be noted that special training and technique is required to prevent contamination by such physical manipulations as touch and breathing.
luer fitting, n: a medical connector having a frustoconically shaped connecting geometry which is in common use in medical practice
luer lock fitting, n: a luer fitting having a locking mechanism whereby a male and female connector are securely, but releasably affixed one to the other
plastic bag, n: a sturdy container made of clear pliant elastomeric material which comprises an opening initially available at one end for product insertion which is sealed thereafter to provide a totally enclosed product shroud, the material being sufficiently pliant to permit digital, in-bag product handling from outside the container interface gasket, n: an elongated hollow cylindrical tube that is sized, shaped and disposed to be affixed along a filter component conduit about a hole in a plastic bag and thereby provide a fluid tight seal port or portal, n: an orifice site where through fluid is communicated (generally associated with a conduit sealingly disposed there through)

proximal, adj: an indicator of a segment of a device being normally close to an object of a sentence describing its position radiation, n: generally gamma radiation imposed with sufficient intensity and time to sterilize a product to a desired SAL.

SAL n: Sterilized Assurance Level subkit, n: a group of parts provided as a unit and considered to be a kit when provided alone but a lesser kit form when provided as a part of a more inclusive kit which is packaged with additional items tray, n: a vial or bottle and cap container wherein parts are stored and transported; for the case of the current invention, the tray is considered to provide special a movement restrictive interface to each vial or bottle and cap unitized, adj: a plurality of separate parts permanently joined to be handled and used as a single unit vial, n: an eye drop bottle

BRIEF SUMMARY AND OBJECTS OF THE INVENTION

In brief summary, this novel invention alleviates all of the known problems related to mixing, dispensing and providing a sterile liquid product for delivery into a field environment. It is important to note that preparation of autologous blood eye drops, involves mixing a measured volume of patient serum with a volume of normal saline determined by prescribed serum/saline concentration and acquired patient serum volume. Though other methods for product processing may be accomplished within the scope of the instant invention, preferred devices and processes are disclosed hereafter for clarity of enablement.

Commonly, autologous eye drop products, as mentioned supra, are often produced by being sterilized by filtration and mixed under a fume or laminar flow hood in a pharmacy or laboratory facilities. For products which are required to be sterilized and mixed in a field environment, remote from such facilities, lack of a fume hood or other sterility control capability currently prohibits wide-spread production of autologous blood eye drops. It is for the purpose of fulfilling this need that an inventive methodology based upon a novel subkit is disclosed herein.

The core items of this subkit are a conventional commercial plastic bag, having an accessible opening, which is closed and sealed after subkit assembly, a sterilizing filter component which is affixed to the bag via a sealed portal to provide a solitary sterilizing fluid pathway to components inside the so closed bag, eye drop bottles and associated caps, and a tray for providing bottle containment and retention throughout the eye drop preparation process. To assure product sterility, the bag and enclosed contents are sterilized after assembly and prior to use. Once sterilized, the only passageway inside the sealed bag is through the filter component. Therefore, all product inside the bag remains sterile for all subsequent procedures until the bag is opened.

For the instant invention, the subkit is delivered as part of a larger kit which additionally comprises two empty conventional medical syringes having male luer fittings, a female/female luer fitting component which is affixed to one of the two empty syringes, a blood collection tube transfer barrel and an accessible volume of normal saline (preferably provided as pre-filled saline syringes). All of the additional parts may be provided clean, rather than sterile, as all fluid which is communicated into the plastic bag is sterilized by passing through the filter which provides the only entry pathway into the bag. Note that all parts of both the subkit and larger kit meet a current FDA Convenience Kit Standard which requires all components involved with a medical procedure be previously cleared for medical use.

An exemplary, more detailed description of components of the subkit made according to the present invention is provided as follows:

1. The plastic bag is sufficiently supple and impenetrable to permit digital manipulation of items disposed therein via digital contact only with the bag exterior and has an accessible opening for displacement of the articles into the bag before the opening is closed and sealed, sufficient material disposed about the opening to permit sealing and an exterior surface which completely envelopes and protects sterility of articles disposed therein. Bag and articles therein should be predisposed to digital manipulation via the bag exterior and should be radiation stable.

2. A filter component comprising a sterilizing grade filter and two opposing elongated conduits having connecting fittings at ends remote from the filter. One of the conduits, is displaced through a tight fitting hole in the bag. A gasket seal is disposed about the conduit/hole interface, providing a hollow conduit as the only fluid access pathway into the bag after the bag opening is sealed. Note that the pathway leads to the filter through which all fluid must pass, thereby assuring that no non-sterile material can be introduced into the bag beyond the filter.

3. At least one bottle comprising an open orifice provided for displacing eye drop liquid there through.

4. A cap for each at least one bottle, the cap being able to be affixed to the bottle while in protective enclosure of the bag to provide a protective seal about the bottle orifice, such that when attached to the bottle and thereafter removed from the bag, following liquid transfer, product sterility is assured. As cap to interior bag surface interface may not have a frictional coefficient which promotes easy digital access and handling within the bag, each cap is provided with a grasping surface treatment which modifies the coefficient of friction between bag and cap and thereby permits facile digital displacement of each cap.

5. A tray having cavities for each bottle and associated cap. Each bottle cavity being sized and shaped to securely engage a bottle through shipment and strictly restrict bottle rotation while a cap is being affixed thereto. Further, each such cavity is disposed to affix retention forces at each bottle bottom, thereby, permitting bottles to be "popped" free after the tray is displaced from the bag. Similarly, each cap cavity is sized and shaped to retain a cap until digitally accessed for capping a bottle while having retaining forces disposed at the bottom thereof to permit the cap to be "popped" free for easy access.

One of the compelling purposes for basic convenience kits resulting from this invention is providing fluid flow through an associated sterilizing filter. As liquids to be mixed in a field environment can be expected to be compromised and/or contaminated, it is critical that every so-employed liquid is passed through such a filter and sterilized before being displaced into the bag. In the case of the instant invention, retention of sterility throughout dispensing and mixing is equally as important. For this reason, all kit mixing, sterilization and subsequent packaging functions are performed within the closed plastic bag which retains such sterility until reopened. It is important to note that digital facility of kit use is also very important. As a consequence, it is preferred to use a bag which comprises a snap or peel open seal for access after product being transferred and sealed in capped bottles. However, it is not enough to maintain liquid sterility only while the product is inside the bag. The product must be shielded and disposed in closed container before displacement from the bag.

Given the subkit contents and additional parts which make up the larger kit, the method for preparing autologous blood eye drops is as summarized in table 1, below:

TABLE 1

| Step # | Step | Comment |
|---|---|---|
| 1 | Using conventional procedures, acquire a predetermined volume of blood from a patient for which a prescription has been provided for receiving eye drops made according to the instant invention. | (It is currently preferred to draw blood into evacuated tubes (such as a Becton Dickenson Corporation Vacutainers ™). |
| 2 | Separate serum from other blood components | Centrifuging is the preferred method |
| 3 | Collect serum into a single container in which the total volume of available serum can be measured | A preferred method for collecting is accomplished by connecting a blood collection tube and transfer barrel to an empty conventional medical (hereafter referenced as the "serum syringe"). These items and other non-subkit items are provided as part of the larger kit mentioned supra. |
| 4 | After collecting all serum from the evacuated tubes, measure the amount of serum collected and determine volume of normal saline to mix with the serum. | Eye drop dose determination (i.e. amount of serum acquired to be mixed with a predetermined volume of saline to yield a prescribed concentration of a blood/serum mixture for a given patient prescription) will likely vary from procedure to procedure, therefore, it is necessary to determine both volume of serum available and amount of saline to be used. The amount of saline to be added to the blood can be calculated using a novel dosing chart, disclosed hereafter |
| 5 | Displace, for delivery, the determined volume of normal saline into a measurable container. | It is preferred to draw the required volume from the larger kit provided pre-filled saline syringes into the originally empty syringe affixed to the female/female connector (saline syringe). |

TABLE 1-continued

| Step # | Step | Comment |
|---|---|---|
| 6 | Mix the collected serum with the measured volume of saline | Mixing is preferably accomplished by transferring all of the contents of the saline syringe into the serum syringe and then displacing contents of the two syringes back and forth at least three times, ending with all of the contents disposed within the serum syringe. |
| 7 | Access the subkit. | The subkit is preferably packaged in a separate casing for safety assurance |
| 8 | Prepare subkit for use | If filter is capped, remove cap. To align the tray with the filter, grasp the exposed portion of the filter and displace it upward relative to the tray, thereby centering the tray and increasing the volume of air inside the bag. Note: All fluid entering the bag is filtered so the SAL state of the bag is not challenged and the filter will not pass gas once wetted. |
| 9 | Deliver a desired volume of the mixture through the filter into each bottle | 11. Separate the saline and serum syringes and affix the serum syringe to the filter fitting for sterilizing the mixture by delivering through the filter. Note: Suppleness of the bag permits digital direction of the filter outlet (spout) toward each targeted bottle orifice |
| 10 | Displace and offset the filter and fitting-less syringe away from the tray such that bottle caps can be digitally accessed. | Once the bottles are filled, the filter parts internal to the bag are displaced away from the tray to permit capping of the bottles. |
| 11 | Cap each bottle | Each cap is individually digitally accessed via the bag exterior. A surface treatment of the cap provides a sufficiently frictional interface between cap and bag to permit each cap to be "popped" from the tray and affixed to an associated bottle. Preferably, each cap is affixed to the bottle by a threaded attachment requiring cap rotation relative to a bottle which is kept stationary by being snugly held within a cavity of the tray. |
| 12 | Breach the bag to access the sealed bottles | Once the bottles are capped and so sealed, the eye drop product is protected even when displaced into a contaminating environment. Thus the bag can be breached with safety, permitting access to individual bottles. |

To show by example, a comparison of advantages and disadvantages relative to employing a convenience kit used according to the present invention versus using a laminar flow hood, for a sterile transfer process, distinctions are summarized in the following two tables (i.e Tables 2 & 3).

Table 2 summarizes a comparison of general factors related to preparing an eye-wash product using a laminar flow hood and the convenience kit.

TABLE 2

| Parameters | Laminar Flow Hood | Present Invention |
|---|---|---|
| Number of packages to open | 15 | 1 |
| Filter | .2 micron - small tip | .2 micron - high flow |
| Maintenance of sterility | Technique dependent | All items in bag and entering bag are pre-sterilized - virtually impossible to contaminate accidentally |

TABLE 2-continued

| Parameters | Laminar Flow Hood | Present Invention |
|---|---|---|
| Likelihood of product contamination | Low | Remote |
| Receiving vessel stability | Usually no special stabilizers used | A stabilizing receptacle can be provided within the bag |
| Injection into receiving vessels | Filtered liquid through a filtered air stream | Sterilized by filter before dispensing into a sterile field |
| User steps | 42 | 24 |
| Ease of use | Simple with proper training | Simpler with conventional technique |

Table 3 compares a current process of producing an eyewash product to a like product production using a convenience kit made according to the present invention.

TABLE 3

| Parameters | Conventional | Present Invention |
|---|---|---|
| Open Packages | 15 | 1 |
| Set up receiving vessels | 4 | 0 |
| Draw serum into syringe from vacutainers | 9 | 9 |
| Purge air from syringe | 1 | 1 |
| Draw saline into delivery syringe | 3 | 3 |
| Mix | 1 | 1 |
| Attach filter to syringe | 1 | 1 |
| Dispense into four receiving vessels | 4 | 4 |
| Cap vessels | 4 | 4 |
| Total | 42 | 24 |

Accordingly, it is a primary object to provide convenience kit methods and apparatus for transferring and sterilizing mixed eye drop liquids to, thereby, provide a packaged, sealed, aseptic product in a potentially contaminating environment.

It is a major object to provide a kit (i.e. subkit) which can be used to sterilize, mix and protectively seal for safety a sterilized product for delivery into a contaminating environment without use of a laminar flow hood.

It is a principle object to provide methods for a portable apparatus which can be used for preparing and delivering eye drops sterilized to a predetermined SAL within a contaminating environment.

It is an object to provide methods and apparatus for preparing and using convenience kits which can be used for sterilizing and delivery of autologous blood-based eye drops in home care situations.

It is an object that a sectioned tray, having at least two recesses wherein eye drop bottle parts are stored and transported as a sub-kit and securely affixed therein for eye drop liquid dispensing and bottle capping to provide a seal for keeping the liquid in a sterile state.

It is a fundamental object to provide a bag which is sealable for maintaining contents sterile therein and able to be opened for access to products mixed and sterilized therein.

It is a crucial object that connected parts disposed in the inner bag be permanently securable to reduce line connections and disconnections after sterilization.

It is another critical object that such adjoined parts be un-releasably affixed (unitized) to preclude separation in subsequent transport and storage.

It is another major object that bagged parts of a convenience kit made according to the present invention be digitally accessible such that liquid sterility protecting caps can be securely affixed to vessels before perforating the bag barrier.

It is yet another critical object to select items which are gamma stable for purposes of sterilization within the bag.

It is still another object to provide a means for transporting and storing filled eye drop bottles in a controlled environment for stability of product sterility and medical efficacy. These and other objects and features of the present invention will be apparent from the detailed description taken with reference to accompanying drawings.

BRIEF DESCRIPTION OF THE DRAWINGS

FIG. 2A is a perspective of a section of tubing for use as a sealing interface gasket having predetermined length and internal diameter relative to the filter component seen in FIG. 2.

FIG. 2B is a perspective of a segment of the bag seen in FIG. 2 with a portion of the filter component having pierced the bag and disposed snuggly within a hole formed therein.

FIG. 9 is an exploded perspective of an evacuated tube blood draw vessel seen in FIG. 8 and a tube access barrel used to mete out blood or blood constituents from the vessel.

FIG. 10A is a perspective of a combination of a medical syringe seen in FIG. 10 affixed to an evacuated tube access barrel wherein a blood draw tube is inserted for selectively accessing blood constituents.

FIG. 12 is a "dosing" chart comprising indicia from which a desired volume of saline can be derived for mixing with predetermined volume of serum for producing a dose of eye drops.

FIG. 16 is a perspective of the assembled key kit, seen in FIGS. 15 and 16, with the syringe seen in FIGS. 10 and 11 containing a serum/saline mixture and affixed to the filter component of the filter appliance for dispensing liquid into bottles thereby.

FIG. 19 is a perspective of an insulated pouch for storing and transporting capped bottles (seen in FIG. 18) after displacement from the plastic bag and the tray.

FIG. 20 is a perspective of a "freezer pack" used to maintain a desired temperature inside the pouch seen in FIG. 19.

DETAILED DESCRIPTION OF THE ILLUSTRATED EMBODIMENTS

Reference is now made to the embodiments illustrated in FIGS. 1-20 wherein like numerals are used to designate like parts throughout. For parts which are similar but not the same as parts originally specified with a given number, a prime of the original numbers may be used.

This inventive method is specifically dedicated to preparing autologous blood serum eye drops. While inventive properties disclosed may be applied throughout a wide variety of applications, the following description is singly focused on eye drop production.

Kit Preparation Steps

Figure 1:
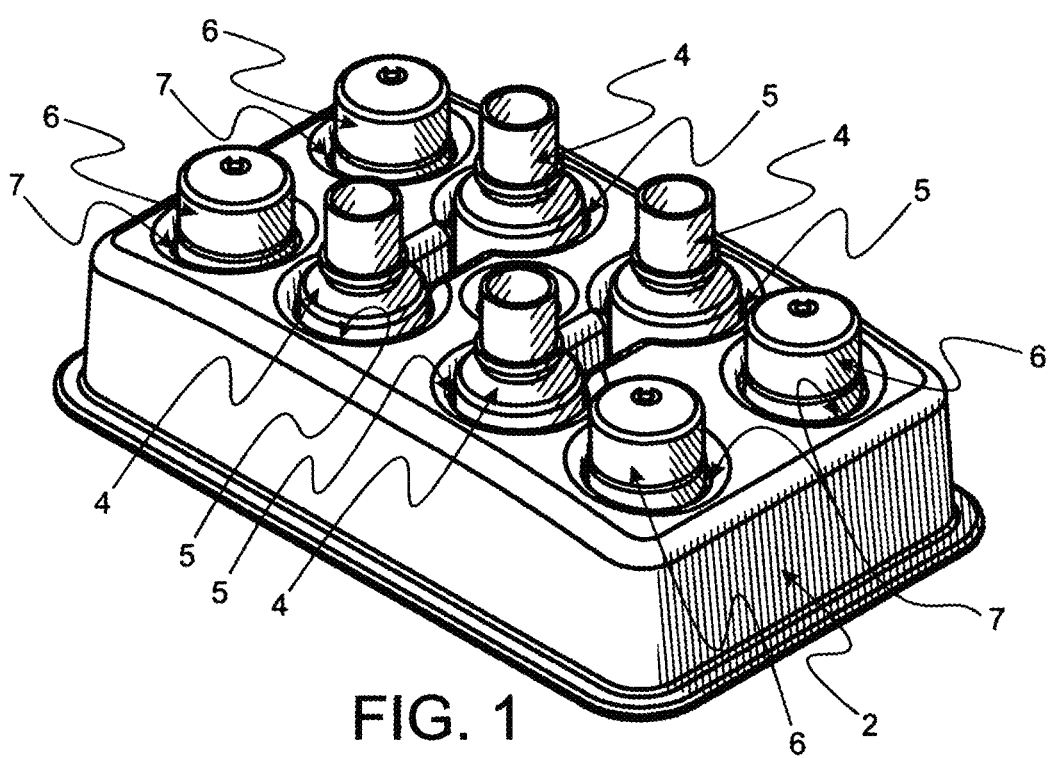
FIG. 1 is a perspective of a tray made according to the instant invention with cavities of predetermined shape and size filled with caps and bottles which are examples of items employed for filling and capping eye drops to preserve sterility thereof.

In FIG. 1, a tray 2 is seen wherein a plurality of eye drop bottles, each generally numbered 4, are disposed within cavities, generally numbered 5, and associated bottle caps, generally numbered 6, are disposed in cavities, generally numbered 7. Tray 2 is a key element of the instant invention providing a stabilizing base for transport and securing bottles 4 and caps 6 as disclosed in detail hereafter.

Figure 1A:
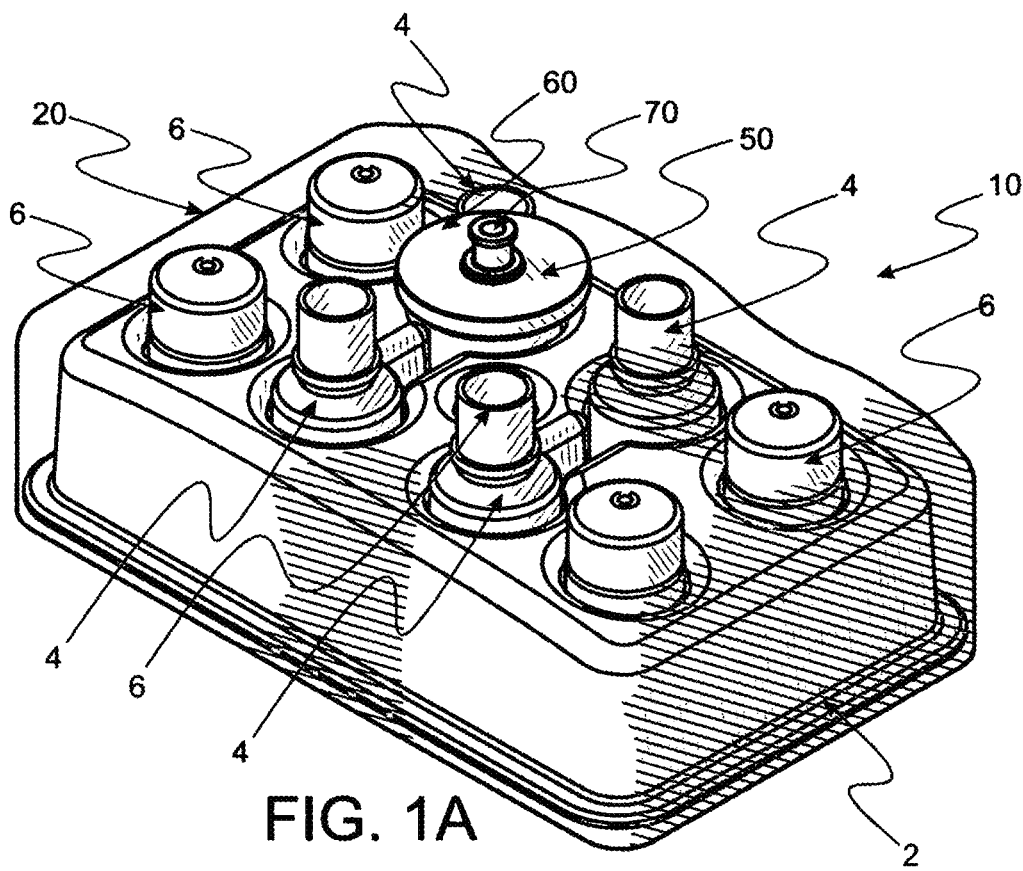
FIG. 1A is a perspective of a perspective of an assembled key kit made according to the present invention, the kit comprising a filter appliance, a portion of which is seen disposed outside a plastic bag, items enclosed within the bag being the tray seen in FIG. 1 securely holding a plurality of bottles and bottle caps.

Reference is now made to FIG. 1A wherein an assembled convenience kit 10 made according to the instant invention is seen. A preferred clear plastic bag 20 is seen to completely envelope a plurality of bottles 4 and associated caps 5 disposed and restrained in a tray 2. To be ready for use, kit 10 has been sterilized to a predetermined SAL. A filter appliance 50 has been disposed through a singular hole in bag 20 (not seen in FIG. 1). Filter appliance 50 comprises a filter component 60 and the only fluid access path 70 into bag 20. Filter component 60 is preferred to be a 0.2 micron sterilizing filter which assures that all fluid displaced along path 70 is sterilized, thereby assuring everything within bag 20 remains sterile in any environment until bag 20 is opened. Filter components, such as filter component 60 are widely used and commercially available for sterilizing fluids in contemporary medical practice.

Figure 2:
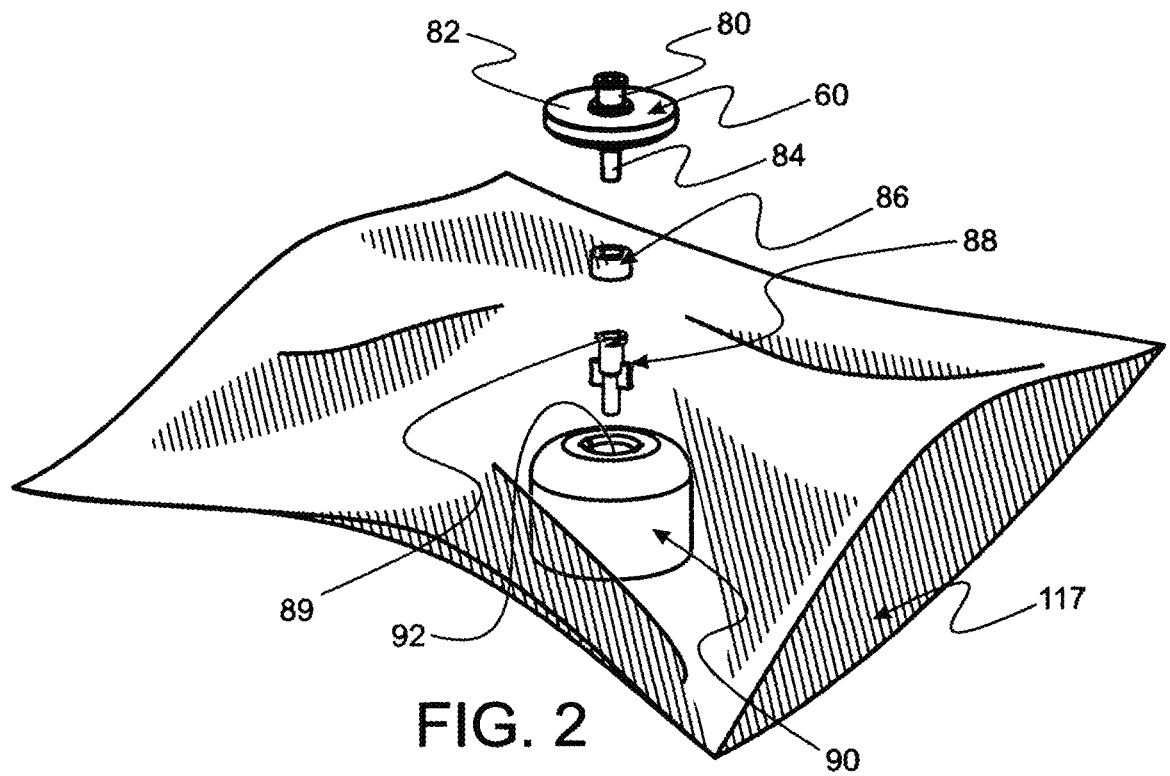
FIG. 2 is a perspective of the plastic bag and filter appliance parts, seen in FIG. 1A, but before assembly, the bag having an open end and a filter component seen to be disposed outside the bag and associated filter appliance and bag sealing components with an assembly tool disposed within confines of the bag.

Reference is made to FIG. 2 wherein a sequence for assembling filter appliance 50 to bag 20 is seen. Therein, filter component 60 is seen to comprise a female luer lock fitting 80, an increased radius housing 82, which contains the 0.2 micron filter (not shown), and a male luer fitting 84.

As seen in FIG. 2B, male luer fitting 84 comprises a distal end 84' which is diminished sufficiently in size to permit fitting 84 to pierce bag 20, seen, in part, as section 20", forming a hole, therein, about fitting 84. Material characteristics of plastic bag cause hole edges to reluctantly give way, resulting in the hole circumference snugly fitting about fitting 84 with no laterally extending tear.

Figure 3:
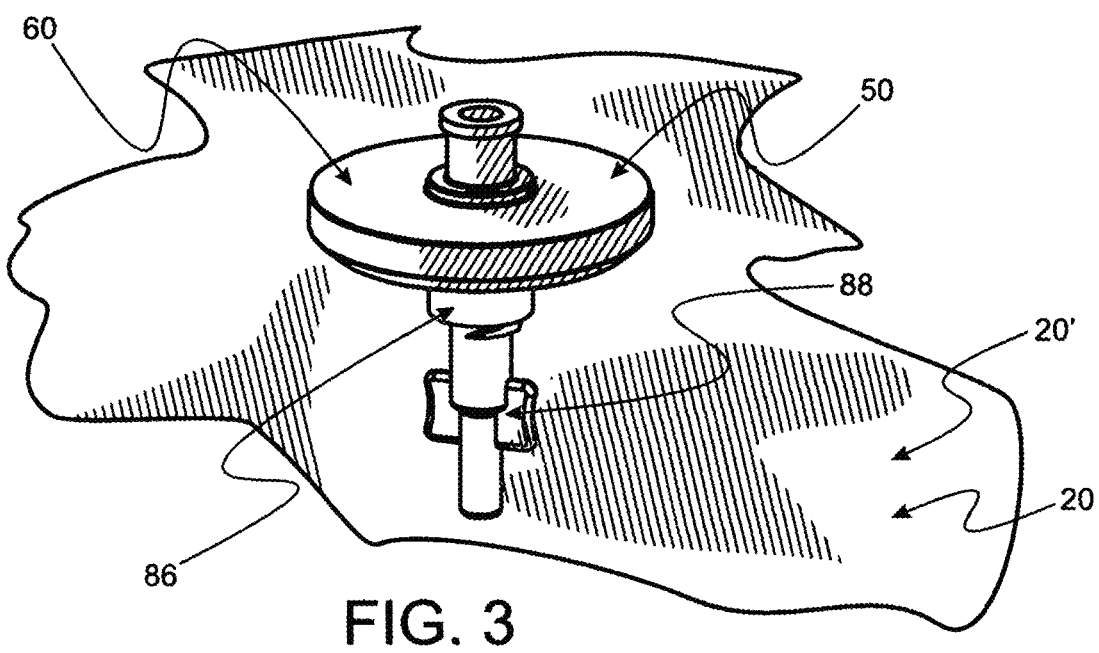
FIG. 3 is a perspective of a segment of the bag seen in FIG. 2, similar to the segment seen in FIG. 2B, with a portion of the filter component disposed outside the bag and another portion disposed through an unseen orifice disposed in the bag (but unseen) with components affixed to the inside portion to seal about the orifice.

Referencing again FIG. 2B, disposed directly below housing 82 is a section 86 of tubing sized and shaped to provide a gasket about the hole through which fitting 84 is disposed and about fitting 84. Cylindrical shape of tubing section 86 is seen in FIG. 2A. A female luer fitting 88 is disposed directly below tubing section 86. Female luer fitting 88 is disposed to provide compressive force against tubing section 86 such that tubing section 86 acts as a gasket against the hole in plastic bag 20. Preferably, fitting 88 is adhesively affixed to fitting 84. An assembly tool 90 comprising a patterned hole for stabilizing fitting 88 is preferably used when fitting 84 as displaced into fitting 88 for attachment. A fully assembled filter appliance 50 is seen in FIG. 3 disposed through a hole in a segment 20' of bag 20.

Selection of an effective eye drop bottle is critical to the safety and effectiveness of the instant invention. As such, the eye drop bottle must be able to be securely capped and closed while being disposed within bag 20. Also, because a prolonged period of time (e.g. four to six weeks) may pass from time of mixing and bottle filling until use, a desired product SAL must be maintained until use. For this reason, an eye drop bottle (called Novelia® (Novelia)) commercially available from Nemera, an international company originated in France, is preferred for use in products made by the instant invention. Nemera states the following concerning Novelia:

> Preservatives have been shown to be harmful to the eye and can lead patients to discontinue or skip treatment to avoid irritation and discomfort. The new multidose ophthalmic packaging Novelia avoids the need for preservatives in the drug by preventing contamination of unpreserved formulations. Novelia represents a major innovation in ophthalmic drug delivery by providing a preservative free alternative for chronic treatments in a patient friendly package. Novelia has been well accepted by patients in over 45 countries worldwide, including U.S., European, Latin American and Asian countries. It is used for packaging drug products as well as medical devices. The key benefit for patients is that it can be used as a 'classic' multidose eyedropper. This device is able to calibrate droplets, which improves compliance. Its blue tip allows better precision when targeting the eye and bottles are easy to squeeze. Novelia is also more sustainable and affordable than unit-doses, and easier to carry.
> 
> For ophthalmic pharmaceutical companies, Novelia offers major advantages:
> 
> 30% controlled and safe thanks to patented PureFlow® technology
> 
> Functional with emulsions, suspensions and solution up to high viscosities
> 
> Compatible with most existing filling lines (screw cap)
> 
> The key requirement for such a device is microbiological sterility; Novelia has been tested and confirmed for content sterility and drop non-contamination for treatment duration (90 days). Novelia represents a major innovation in ophthalmic drug delivery devices by providing patients with a preservative-free alternative for chronic treatments, with a patient-friendly package.

Figure 5:
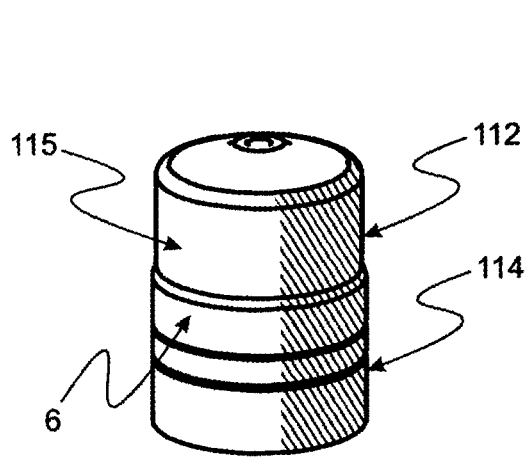
FIG. 5 is a perspective of a cap for closing and providing a seal to protect contents of the bottle seen in FIG. 4.
Figure 4:
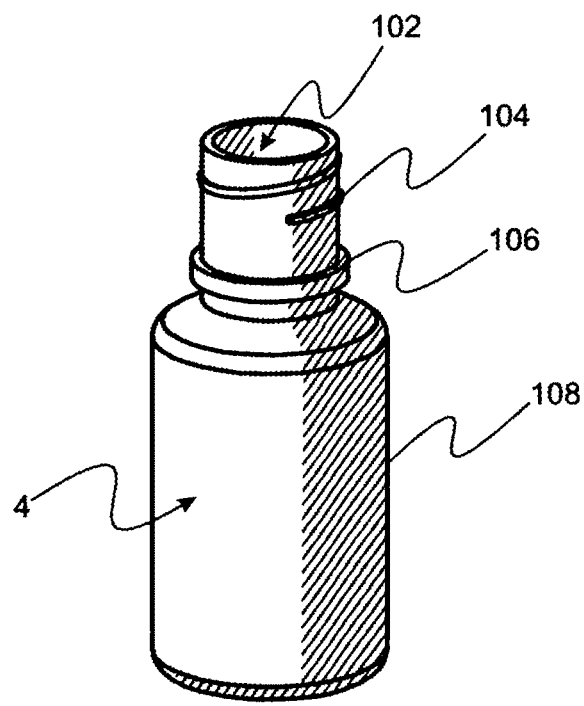
FIG. 4 is a perspective of a bottle to be disposed within the tray seen as in FIGS. 1 and 1A.

Reference is now made to FIGS. 4 and 5 wherein elements of the preferred bottle 4 and cap 6 for the invention are respectively seen. In FIG. 4, eye dropper bottle 4 is seen to comprise an open, superiorly disposed filling orifice 102, a raised thread pattern 104 whereby cap 6 is affixed to bottle 4 and a locking ring 106 whereby cap 6 is securely locked to bottle 4 by continuing rotation about pattern 104. Bottle 4 also comprises a large vessel portion 108 which is sized and shaped to hold a predetermined volume of product.

Cap 6, seen in FIG. 5, comprises two basic sections, a superior section 112 and an inferior section 114. Superior section 112 is formed as a displaceable lid which is attached via a threaded interface (not shown) to section 114. When section 112 is disposed in abutting contact with section 114 and securely affixed to bottle 4, bottle 4 is sealed closed. Cap 6 is rotated about the threaded interface between section 112 and 114 to open bottle 4 for eye drop dispensing as disclosed by Nemera (supra). A locking interface (not shown) within section 114 securely affixes cap 6 to bottle 4 when cap 6 is fully turned about thread pattern 104 (see FIG. 4) and thereby closing bottle 4 orifice 102. For purposes, disclosed in detail hereafter, outer surface 115 of section 112 is treated to change the coefficient of friction between surface 115 and bag 20 interior surface 117 (see FIG. 2).

Figure 6:
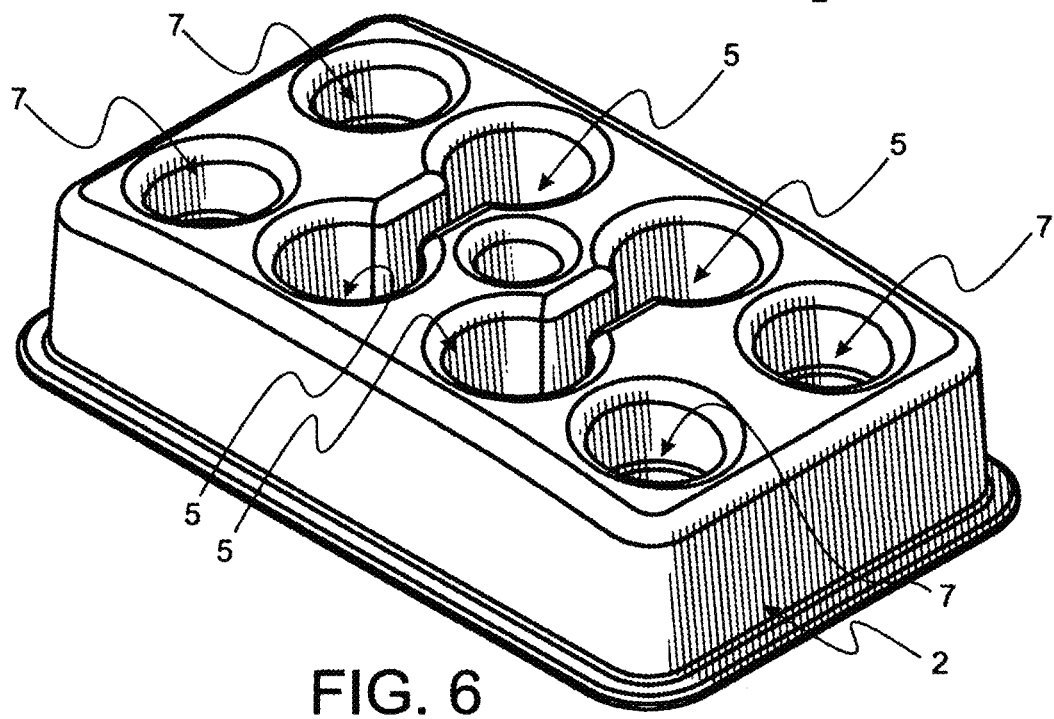
FIG. 6 is a perspective of the tray seen in FIG. 1 with a plurality of empty cavities.

Reference is now made to FIG. 6 wherein tray 2 is seen with a plurality of empty cavities generally numbered 5 and 7. Each cavity 5 is sized and shaped to provide inferiorly disposed pressure about an inserted bottle 4. Such inferiorly disposed pressure restricts bottle rotation when cap 6 is affixed to bottle 4. Inferior application of retaining pressure permits bottle 4 to be "popped" free from tray 2 for independent use after being displaced from bag 20. Each cavity 7, similar to cavity 5, is sized and shaped to retain a cap 6 during transport and before being displaced for capping a bottle 4 while being disposed in bag 20. Further, exterior surface 115 (see FIG. 5) is treated with an overcoat of a substance which substantively increase the coefficient of friction between bag 20 inner surface 117 and section 112. Without such treatment the interface between bag 20 and cap 6 would be "slick" making digital grasping difficult, if not impossible to accomplish. With the treatment, digital displacement of cap 6 is made facile and sure, a feature which is critical to the instant inventive method. Tray 2 is seen to filled with bottles 4 and caps 6 in FIG. 1.

Figure 7:
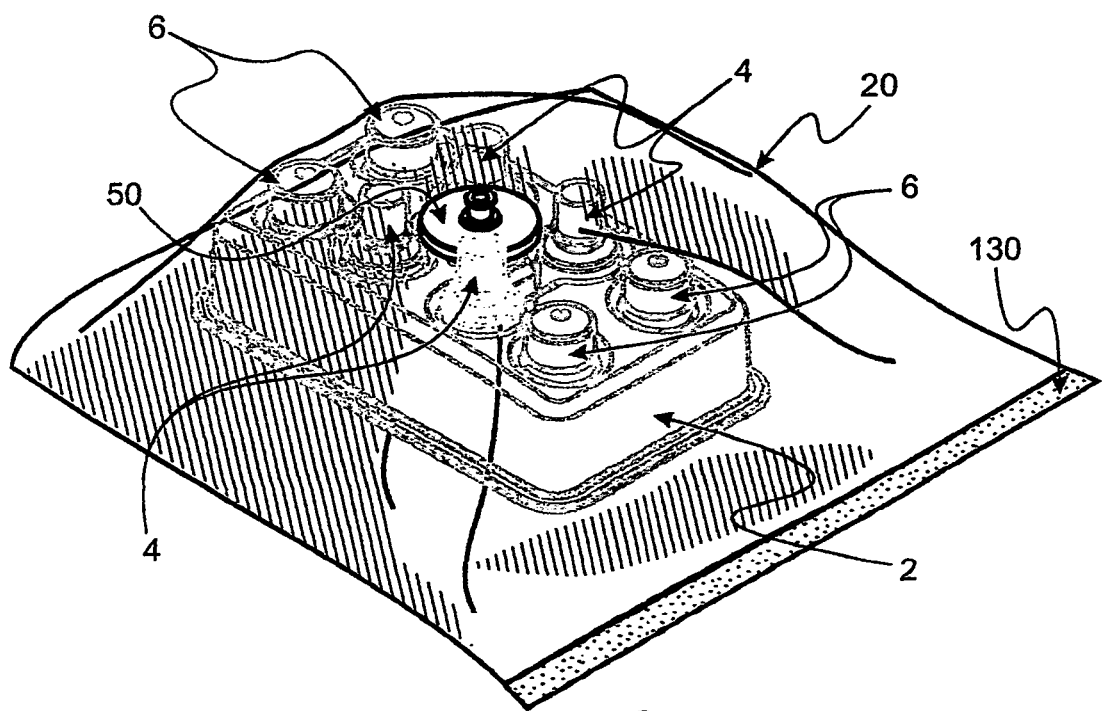
FIG. 7 is a perspective of a bag comprising an affixed filter appliance as seen in part in FIG. 1A and a tray filled with bottles and caps and disposed within the bag, with the open end seen in FIG. 2, closed and sealed.

To complete kit 10 assembly, tray 2 filled with bottles 4 and caps 6 is displaced into bag 20 as seen in FIG. 7. Then bag 20 is securely closed, preferably by a heat seal 130, to complete assembly as a final assembly step of subkit 10. So closed and sealed bag 20 is sterilized along with all contents of convenience subkit 10 contained therein, preferably by gamma radiation. Thus, an enclosed, qualified SAL space, inside bag 20, which is only accessible through sterilizing filter 60 through pathway 70 (see FIG. 1A) is created according to the instant invention.

Eye Drop Preparation Steps

Figure 8:
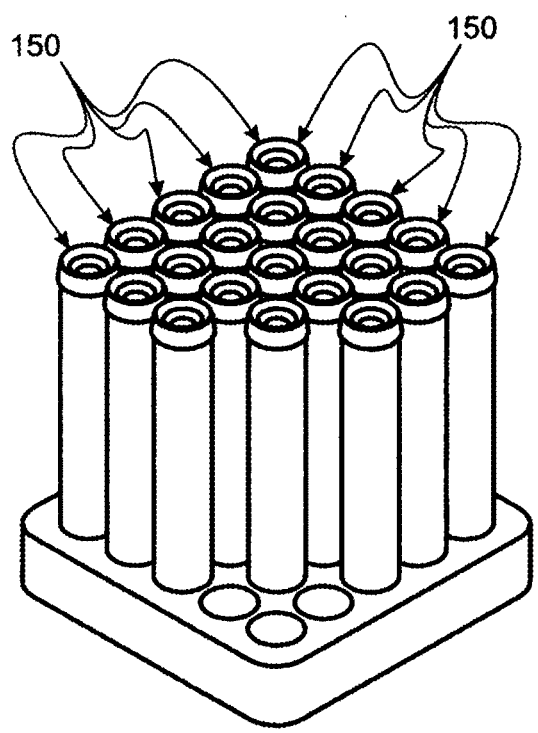
FIG. 8 is a perspective of a plurality of evacuated tube blood draw vessels (e.g. Becton Dickinson Vacutainers™).

Blood is preferably accessed from a patient for preparing autologous blood eye drops; using Becton Dickinson Vacutainers™, samples of which are commonly numbered 150 and seen in FIG. 8; by conventional technique.

Figure 10:
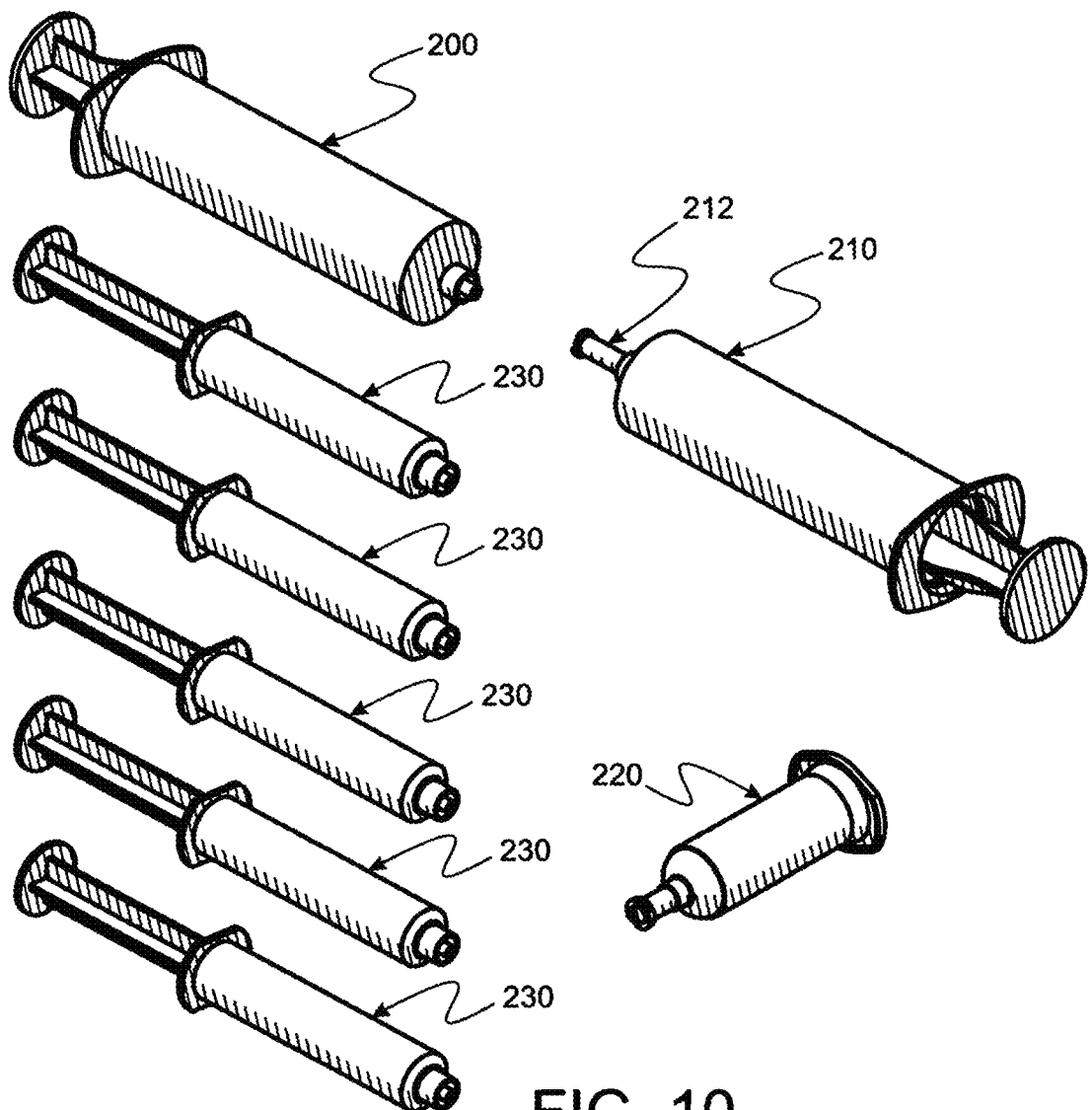
FIG. 10 is a perspective of separate items used in a larger kit to support the key or subkit.

Items which are provided as part of a larger kit are seen in FIG. 10. These items comprise:

1. A first conventional medical syringe 200 which is specified to have a capacity for accessing and containing the total liquid volume of all vessels 108 of bottles 4 in convenience kit 10.

2. A second medical syringe 210 having the same liquid volume as syringe 200 and being securely affixed to a female/female fitting 212.

3. A Vacutainer™ access barrel 220.

4. A plurality of conventional pre-filled normal saline syringes, generally numbered 230.

Each of items listed in 1-3, above can be provided clean (as opposed to sterile) because all fluid which contacts these items is sterilized upon being dispensed through pathway 70 of filter component 60 into bag 20. For safety, prefilled syringes 230 should be pre-sterilized. Preparation for filling bottles 4 involves:

1. Prescribing a ratio of serum to saline to be mixed and form a desired (prescribed) mixture which is used as autologous blood eye drops.

2, Following conventional procedures for:
   a. Drawing a prescribed volume of blood from a patient (preferably into evacuated tubes (e.g. Becton Dickinson Vacutainers™), generally numbered 150, as seen in FIG. 8.
   b. Separating patient serum from other blood constituents by centrifuging each evacuated tube 150 and then meting out serum from other blood constituents. For this procedure, a conventional evacuated tube access barrel 232 is preferred to be used (seen in FIG. 9, along with a filled evacuated tube 150' disposed for insertion into barrel 232). Separated serum is drawn into syringe 200 from barrel 232, interconnected, as seen in FIG. 10A.

Figure 11:
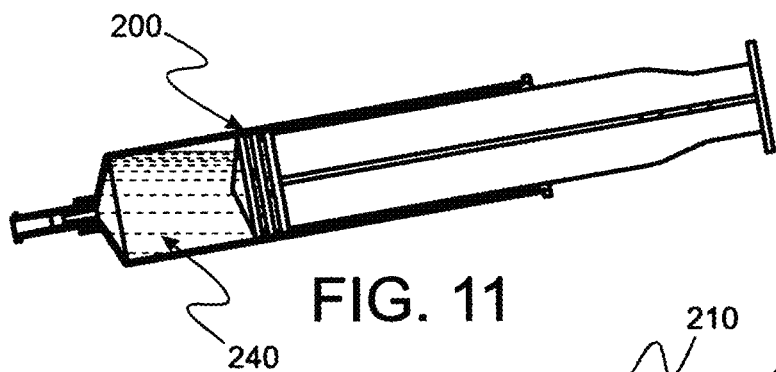
FIG. 11 is a cross section of the conventional medical syringe seen in FIG. 10A, comprising a measurable volume of serum accessed from one or more blood draw vessels.

3. Using conventionally provided indicia (not shown in FIG. 10) on syringe 200 barrel or determining by weight a measure of the volume of patient serum 240 collected in syringe 200 as shown in FIG. 11.

4. Referencing the prescribed saline/serum ratio, determining the amount of saline which must be added to the acquired blood volume to formulate each predetermined dose. Two methods for determining saline volume are currently preferred. However, other methods may be used within the scope of the instant invention. A first method is via a chart 242 such as the one seen, by example, in FIG. 12. As an example, if the dose serum to saline ratio is 20% to 80%, respectively, and the measured amount of serum is 8.4 mL, a value of 8.4 is located under the 20% Serum column heading and a straight line (such as line 244 is drawn from the serum value across to the associated saline value which is, within plotting accuracy, 33.6 mL. If a number processing program, like EXCEL is available the saline volume (mLsal) can be calculated from dose (% ser) and measured serum volume (mLser) by the following equation:

$$mLsal = mLser(100/\% \, ser - 1)$$

Figure 13:
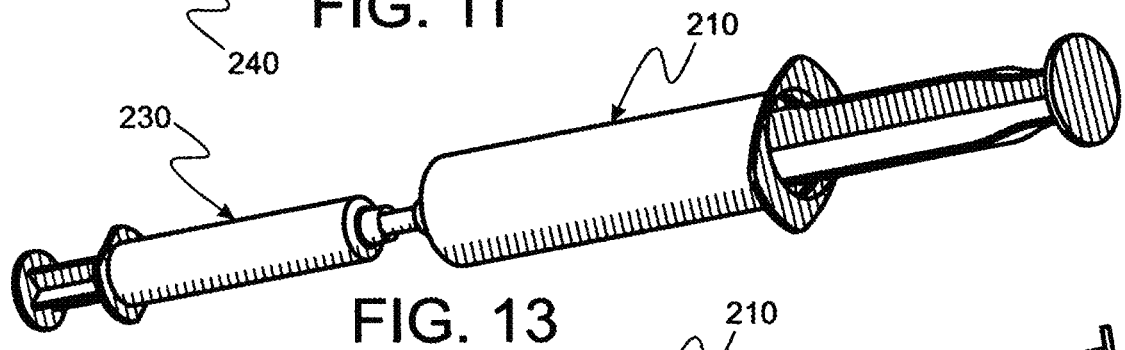
FIG. 13 is a perspective of the conventional syringe affixed to a female/female fitting, as seen in FIG. 10, affixed to a pre-filled syringe for acquiring saline.
Figure 13A:
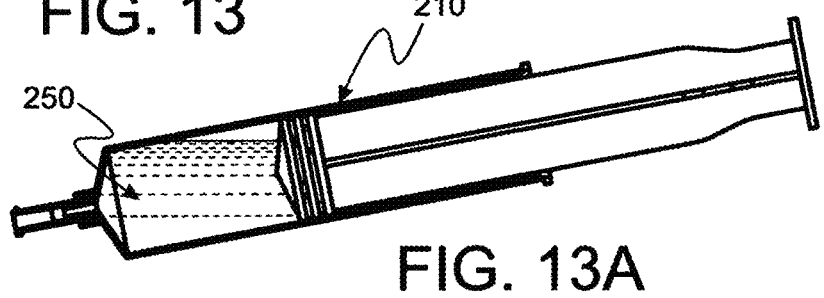
FIG. 13A is a cross section of the medical syringe seen in FIG. 13 with a predetermined volume of saline disposed therein.
partially filled with blood derived 5% normal saline

5. Drawing a determined required dose volume of saline (mLsal) into syringe 210 (see FIG. 10) from pre-filled syringes 230, resulting in syringe 210 being partially filled with saline 250 as seen in FIG. 13A.

Figure 14:
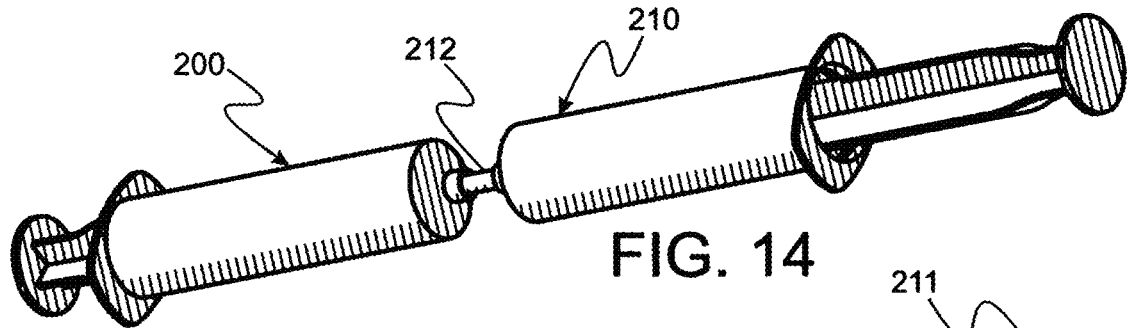
FIG. 14 is a perspective of the syringes seen in FIGS. 11 and 13A affixed together via the female/female adapter.
Figure 14A:
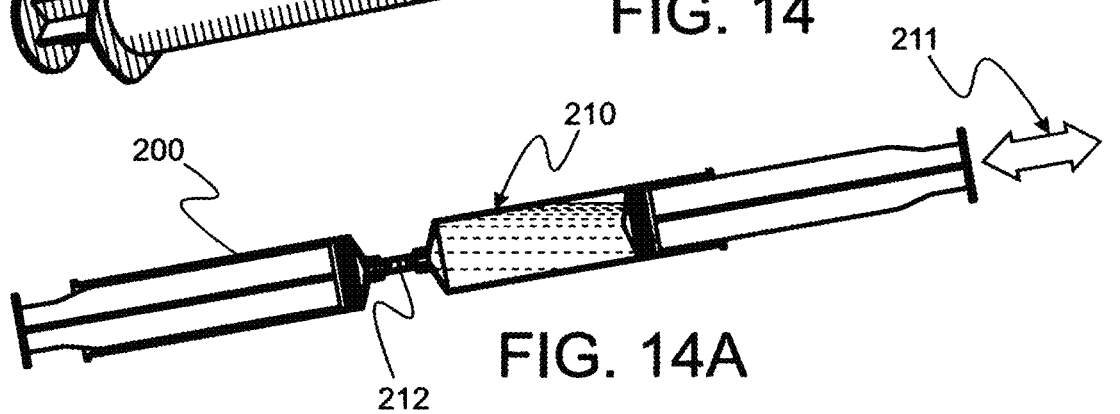
FIG. 14A is a cross section of the syringes seen in FIG. 14 with all liquid displaced into a single syringe and a double arrow disposed to indicate relative displacement of syringe pistons for mixing.

6. Affixing syringe 200 to communicate with syringe 210 as seen in FIG. 14, displace contents of syringes 200 and 210 back and forth, as indicated by arrow 211 in FIG. 14A, a predetermined number of times (at least three times is preferred) to assure adequate mixing of serum and saline, with all of the mixture being displaced into syringe 200 at the end of the mixing cycle.

7. Detaching syringe 200 from fitting 212.

Figure 15:
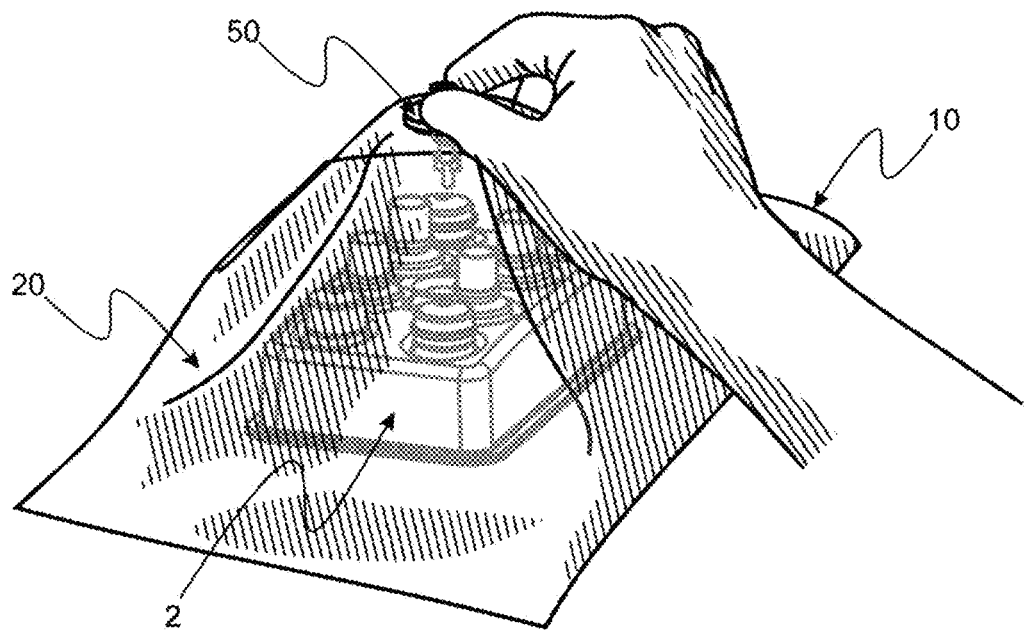
FIG. 15 is a perspective of the assembled key kit, seen in FIG. 1, with the filter appliance upwardly disposed to center the tray disposed therein and to "tent" the bag thereby disposing the filter appliance for dispensing liquid into the bottles.
Figure 15A:
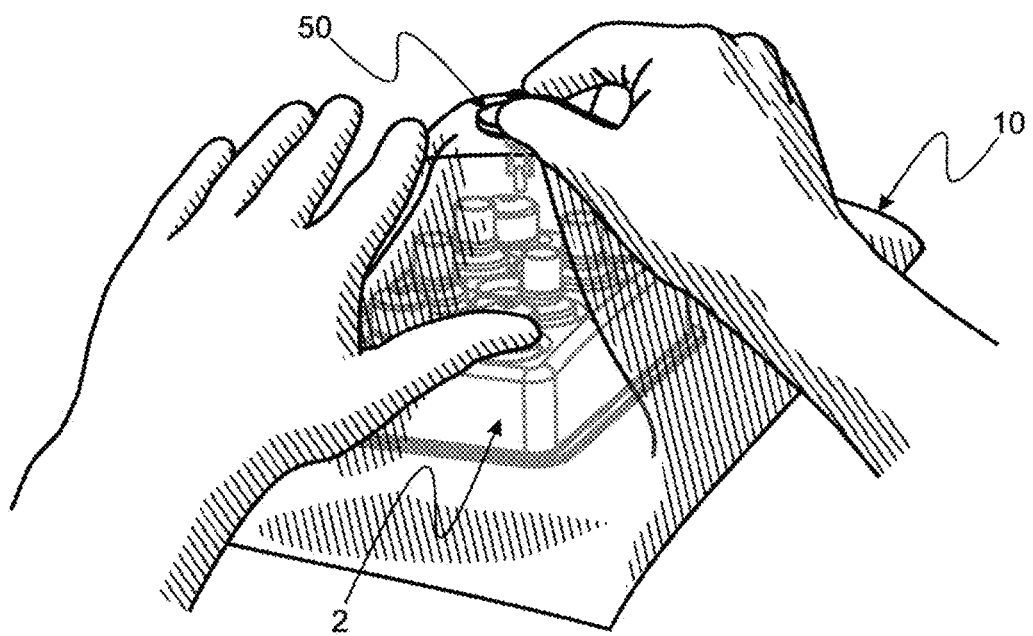
FIG. 15A is a perspective of upwardly displacing and "tenting' the bag similar to the method seen in FIG. 1, but employing an additional hand to aid in centering the associated tray.

8. Acquiring kit 10, which may be disposed as seen in FIG. 1A, and digitally clutching filter component 50, at bag 20 exterior, and displacing component 50 upward, as seen in FIG. 15, "tents" bag 20 for more facile access to items disposed within bag 20. A second hand and may be used in the "tenting" process as seen in FIG. 15A for assuring tray 2 centering.

9. Then, affixing, as seen in FIG. 16, syringe 200 to filter component 60 and dispensing a prescribed volume into each bottle 4 via orifice 102 as shown by example in FIG. 16. Note that suppleness of bag 20 permits digitally guiding filter appliance 50 into communication with each bottle 4 whereupon liquid is efficaciously dispensed through each orifice 102.

Figure 18:
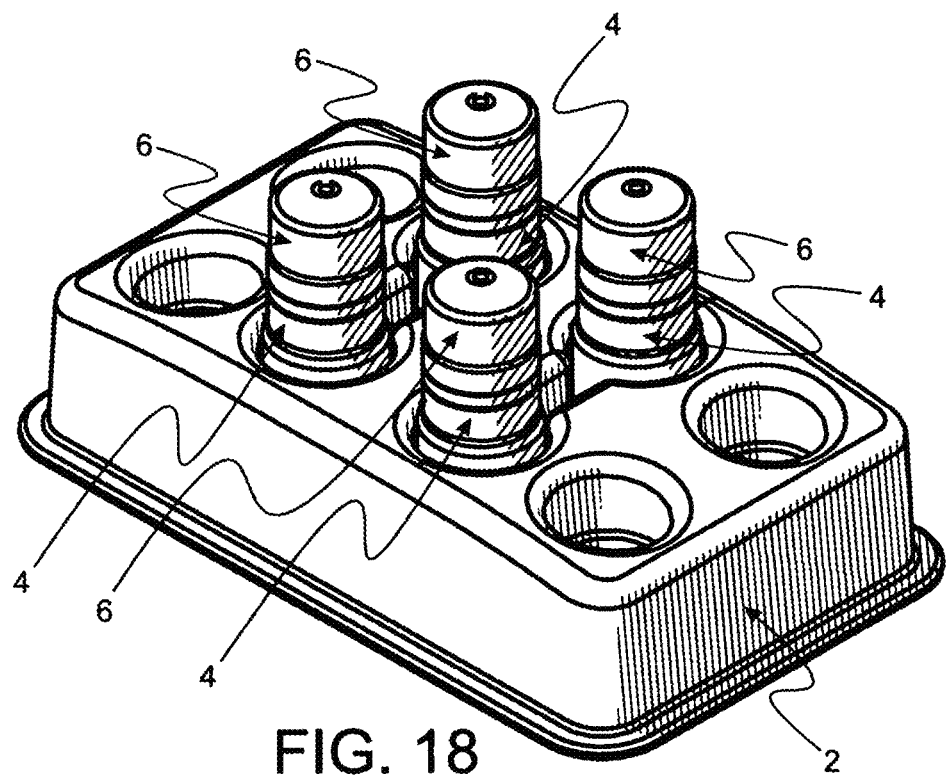
FIG. 18 is a perspective of bottles securely capped for protecting sterility of mixture disposed therein, thus permitting safety in displacing the bottles from the plastic bag.
Figure 17:
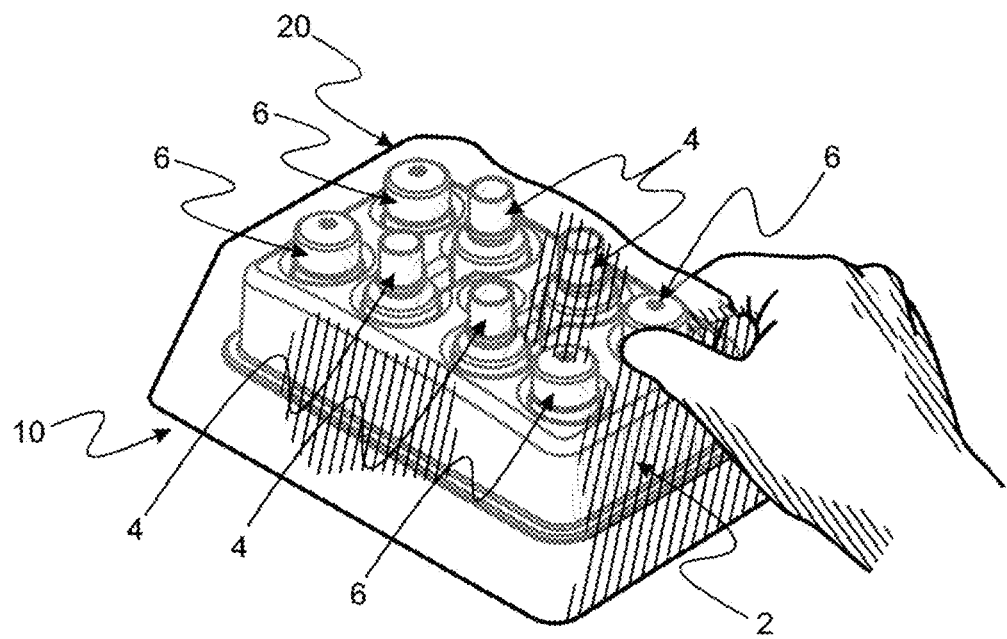
FIG. 17 is a perspective wherein a cap is digitally accessed for removal from the tray for being affixed to a bottle (into which a predetermined volume of serum/saline mixture has been dispensed).
Figure 17A:
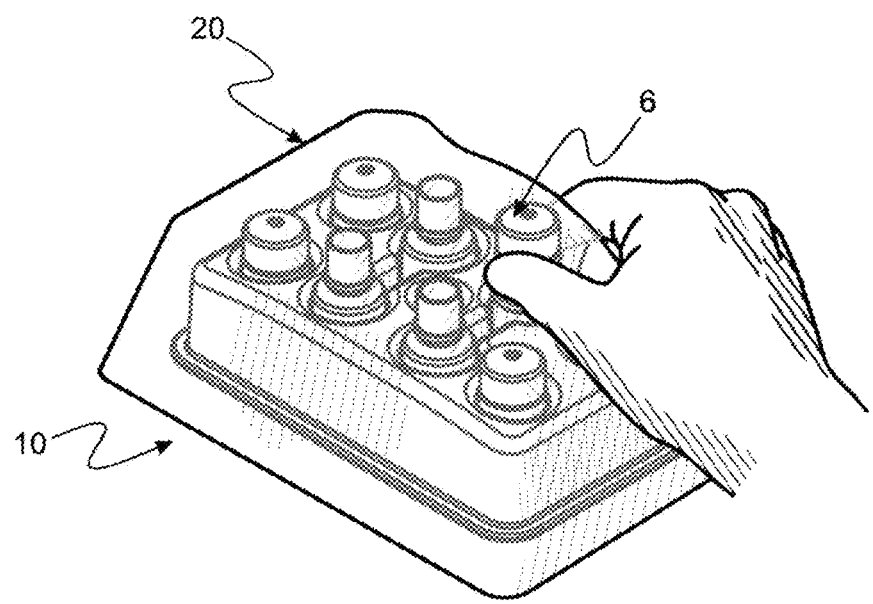
FIG. 17A is a perspective wherein the cap digitally access in FIG. 17 is being digitally affixed to a bottle.

10. Capping each bottle 4. Once every bottle 4 is filled with a prescribed dose, a considered critical step still remains, capping and sealing each bottle 4 for delivering such bottles into an open environment would otherwise likely detrimentally affect SAL of bottle content. To cap each bottle, each cap 6 (see FIGS. 1, 5 and 7) is digitally accessed one-by-one, by external contact through bag 20 as seen in FIG. 17. As stated supra, as molded, cap 6 has an exterior surface 115 which has a very low coefficient of friction, making virgin caps difficult, if not impossible to grasp effectively. To facilitate digital grasping and displacing cap 6, surface 115 (see FIG. 5) is coated with a rubbery material, such as Plasti-Grip by Plasti-Grip, International. Once each cap 6 is displaced in contact with bottle 4 about orifice 102, suppleness of bag 20 permits twisting cap 6 and thereby securely affixing each cap 6 and sealing each bottle 4. It should be remembered that, for ease of digital operation from the exterior of bag 20, each cavity 5, in which bottle 4 resides in tray 2, is sized and shaped to restrain bottle 4 from turning as cap 6 is rotated into a closing and locking position. Note that it is a design characteristic of Novelia to lock cap 6 to bottle 4 as a final action of cap 6 to bottle 4 attachment, resulting in each bottle 4 being securely capped as seen in FIG. 18. Such locking permits section 112 of cap 6 to be later displaced from section 114 for dispensing eye drops.

11. Providing for protecting product outside bag 20. Once all bottles 4 are filled and capped, bag 20 is breached for delivering eye drops to a patient, additional care should be provided for, while the product is sterile to a given SAL, the product contains material which is life based. To aid in maintaining an acceptably sterile state, it is highly recommended that a means for keeping eye drop liquids at a low temperature throughout transport and storage. For this purpose an insulated bag 300 and an associated ice pack 310 (seen in FIGS. 19 and 20, respectively, be provided as part of the larger kit. Such insulated bags and ice packs are commercially available.

The invention may be embodied in many other specific forms without departing from the spirit or essential characteristics thereof. The presently disclosed embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method for preparing a prescribed mixture of medicinal liquids, sterilized to a predetermined SAL, using a portable convenience kit within a potentially contaminating environment away from special equipment used to provide a controlled, sterilized workplace in which prescriptions can be formulated free from contamination, comprising the following steps:

i. providing the convenience kit comprising:
   a. a plastic bag, having an accessible opening for displacement of items therein, being constructed of material which is sufficiently supple and impenetrable to permit digital manipulation of the items from outside the bag, being constructed with sufficient material disposed about the opening to permit sealing the bag to be entirely closed to comprise an exterior surface which completely envelopes and protects sterility of items disposed therein once the bag is sealed;
   b. an appliance comprising a gasket and a filter component which comprises two opposing fluid conducting conduits and a sterilizing grade filter disposed to filter all fluid which is displaced between the conduits, one of said conduits being displaced through a hole in said bag which is sealed closed about the displaced conduit by said gasket;
   c. a combination comprising at least one bottle and at least one associated cap which when securely affixed to said bottle closes a bottle orifice through which liquid is dispensed and thereby provides secure sterility protection for bottle contents;
   d. a tray, which provides stabilizing support, comprising one cavity for each bottle and one cavity for each cap of said combination, each said bottle cavity being sized and shaped to secure an inserted bottle from inadvertent displacement and rotation, and each said cap cavity being sized and shaped for securing a cap in transport and being disposed for facile digital access from outside said bag whereby each bottle is capped by digital access to the cap alone;
   e. sterilizing said bag and contents for a single sterilizing, filling and capping use;

ii. acquiring a predetermined volume in a dispensing vessel of a first liquid to be mixed;

iii. determining a volume of a second liquid to meet a prescribed mixing ratio and acquiring the second liquid in a dispensing vessel;

iv. dispensing a quantity of each first and second liquid through said filter conduits into each bottle to sterilize the quantities and formulate a prescribed mixture;

v. digitally displacing and securely affixing a cap to each bottle by digital access only to the cap; and vi. after all bottles are filled and capped; breaching the bag and extract securely capped bottles containing sterile product for use.

2. A method for preparing a prescribed mixture of medicinal liquids according to claim 1 wherein said predetermined mixture comprises an autologous blood serum and saline mixture to formulate autologous blood serum eye drops.

3. A method for preparing a prescribed mixture of medicinal liquids according to claim 2 wherein an acquiring a first liquid to be mixed step comprises acquiring a predetermined blood volume from a patient for whom eye drops are prepared.

4. A method for preparing a prescribed mixture of medicinal liquids according to claim 3 wherein the acquiring a first liquid to be mixed step further comprises processing the acquired blood volume to separate serum from other blood constituents.

5. A method for preparing a prescribed mixture of medicinal liquids according to claim 4 wherein the acquiring a first liquid to be mixed step further comprises displacing separated serum from the acquired volume into a first dispensing container wherefrom a measure of the acquired volume can be made.

6. A method for preparing a prescribed mixture of medicinal liquids according to claim 5 wherein the acquiring a first liquid to be mixed step further comprises ascertaining serum volume.

7. A method for preparing a prescribed mixture of medicinal liquid according to claim 6 wherein an acquiring a second liquid determining step comprises determining a prescribed ratio of serum to saline required for the prescribed eye drop preparation and thereby determining the desired volume of saline in the mixture.

8. A method for preparing a prescribed mixture of medicinal liquid according to claim 7 wherein a dispensing step comprises displacing a proportionate quantity of eye drop preparation into each bottle.

9. A method according to claim 3 wherein said blood acquiring step comprises employing Becton Dickinson Vacutainer™ devices.

10. A method according to claim 3 wherein said blood volume processing step to separate serum comprises centrifuging.

11. A method according to claim 9 wherein said separated serum displacing step involves comprises displacing serum into a conventional medical syringe via a blood collection barrel.

12. A method according to claim 7 wherein said saline volume determining step comprises using a dosing chart.

13. A method according to claim 7 wherein said saline volume determining step comprises calculating desired saline volume from the equation:

$$mlsaline = mlserum * (100/\% serum - 1)$$

wherein "mlsaline" is volume of desired saline in milliliters and "mlserum" is the volume of acquired serum in milliliters and "% serum" is the prescribed serum content in the mixture.

14. A method according to claim 8 wherein said dispensing step comprises using a conventional medical syringe having a female/female connector affixed thereto for communicating with a saline prefilled syringe.

15. A method according to claim 1 wherein said displacing a quantity of each first and second liquid step comprises affixing a first syringe, containing the acquired volume of serum, to a second syringe, containing the desired volume of saline via a female/female connector and accomplishing mixing by delivering contents of the first syringe into the second syringe and then displacing contents of the receiving syringe into the delivering syringe and repeating such displacement a plurality of times thereby achieving a homogeneous mixture within the first syringe before displacement through said filter into the bottles.

16. A method according to claim 1 wherein said dispensing a quantity of each first and second liquid step comprises digitally grasping said filter component and displacing it away from said tray to center said tray within the bag and increase air volume inside said bag before dispensing liquid into bottles.

17. A method according to claim 1 wherein said cap displacing and securely affixing step comprises a preparatory step before said cap is inserted into said tray, said preparatory step comprising treating the exterior surface of said cap with a substance which increases the coefficient of friction between cap exterior surface and bag material to facilitate digitally grasping said cap residing inside said bag.

* * * * *